United States Patent
Prestel et al.

(10) Patent No.: US 9,700,289 B2
(45) Date of Patent: Jul. 11, 2017

(54) HANDLE FOR A MEDICAL INSTRUMENT

(71) Applicant: Richard Wolf GmbH, Knittlingen (DE)

(72) Inventors: Stephan Prestel, Rheinstetten (DE); Ernst Falk, Sternenfels-Diefenbach (DE); Eberhard Körner, Knittlingen (DE); Manfred Boebel, Neulingen-Bauschlott (DE)

(73) Assignee: Richard Wolf GmbH, Knittlingen (DE)

( * ) Notice: Subject to any disclaimer, the term of this patent is extended or adjusted under 35 U.S.C. 154(b) by 302 days.

(21) Appl. No.: 14/354,382

(22) PCT Filed: Oct. 30, 2012

(86) PCT No.: PCT/EP2012/071462
§ 371 (c)(1),
(2) Date: Apr. 25, 2014

(87) PCT Pub. No.: WO2013/064487
PCT Pub. Date: May 10, 2013

(65) Prior Publication Data
US 2014/0303607 A1 Oct. 9, 2014

(30) Foreign Application Priority Data
Oct. 31, 2011 (DE) .................. 10 2011 085 512

(51) Int. Cl.
*A61B 17/00* (2006.01)
*A61B 17/29* (2006.01)

(52) U.S. Cl.
CPC .... *A61B 17/00234* (2013.01); *A61B 17/2909* (2013.01); *A61B 2017/0046* (2013.01);
(Continued)

(58) Field of Classification Search
None
See application file for complete search history.

(56) References Cited

U.S. PATENT DOCUMENTS

2006/0129146 A1* 6/2006 Dycus ................ A61B 18/1445
606/51
2006/0271042 A1* 11/2006 Latterell ............ A61B 18/1445
606/51
(Continued)

FOREIGN PATENT DOCUMENTS

DE 10132358 A1 1/2003
DE 202007007327 U1 7/2007
(Continued)

OTHER PUBLICATIONS

Int'l Search Report issued Jan. 10, 2013 in Int'l Application No. PCT/EP2012/071462.
(Continued)

*Primary Examiner* — Gary Jackson
*Assistant Examiner* — Qingjun Kong
(74) *Attorney, Agent, or Firm* — Panitch Schwarze Belisario & Nadel LLP (57) ABSTRACT

A handle for a medical instrument includes an actuation element, which is arranged on the handle and which is displaceable into at least a first and a second functional position. The actuation element can be moved in a plane transverse to its displacement direction, in each of the first and second functional positions, for carrying out a function. A pivotable actuation lever is arranged in the handle, the actuation lever being coupled in movement to the actuation element for displacing the actuation element into the at least two functional positions.

11 Claims, 6 Drawing Sheets

(52) U.S. Cl.
CPC . *A61B 2017/292* (2013.01); *A61B 2017/2923* (2013.01); *A61B 2017/2929* (2013.01)

(56) References Cited

U.S. PATENT DOCUMENTS

| | | | |
|---|---|---|---|
| 2007/0093790 A1* | 4/2007 | Downey | A61B 17/00234 606/1 |
| 2007/0142833 A1* | 6/2007 | Dycus | A61B 18/1445 606/51 |
| 2009/0240274 A1 | 9/2009 | Boebel et al. | |
| 2011/0106143 A1* | 5/2011 | Boebel | A61B 17/29 606/205 |
| 2012/0080496 A1* | 4/2012 | Schall | A61B 90/92 227/177.1 |

FOREIGN PATENT DOCUMENTS

| | | |
|---|---|---|
| DE | 102009051515 A1 | 5/2011 |
| EP | 1980213 A2 | 10/2008 |
| EP | 2103264 A1 | 9/2009 |
| EP | 2316358 A1 | 5/2011 |

OTHER PUBLICATIONS

Office Action issued Aug. 8, 2012 in DE Application No. 10 2011 085 512.2.

\* cited by examiner

Fig.9 ic # HANDLE FOR A MEDICAL INSTRUMENT

CROSS-REFERENCE TO RELATED APPLICATIONS

This application is a Section 371 of International Application No. PCT/EP2012/071462, filed Oct. 30, 2012, which was published in the German language on May 10, 2013, under International Publication No. WO 2013/064487 A1 and the disclosure of which is incorporated herein by reference.

BACKGROUND OF THE INVENTION

The invention relates to a handle for a medical instrument.

A handle of a medical instrument is usually to be understood as the part of the instrument by which the instrument is manually held and led by a grip part arranged there and on which one or more actuation elements are arranged for carrying out the functions which can be executed with the instrument.

Apart from handles, with whose actuation elements respectively only one function of a medical instrument can be carried out, a medical instrument having a handle is known from German published patent application DE 10 2009 051 515 A1 (counterpart: US patent application publication 2011/0106143 A1), with which several functions can be carried out with one actuation element. This instrument comprises a shank which is arranged on the proximal side of the handle and which is rotatable about its longitudinal axis. A tool which is rotatable relative to the shank is arranged at the distal end of the shank. The handle comprises an actuation element in the form of a rotation wheel, with which on the one hand the shank can be rotated and on the other hand the tool can be rotated relative to the shank. For this, the rotation wheel is axially displaceable in the handle into two functional positions, wherein in a first functional position it is coupled in movement to the shank which can then be rotated by a rotation of the rotation wheel, and in a second functional position it is coupled in movement to the tool which in this functional position can be rotated relative to the shank by rotating the rotation wheel.

The handle of the instrument known from DE 10 2009 051 515 A1 represents a significant improvement compared to handles with whose actuation elements only one function can be carried out in each case, wherein this handle however still does not represent the best possible solution from an ergonomic point of view.

BRIEF SUMMARY OF THE INVENTION

It is the object of the invention, to create a handle for a medical instrument, which comprises at least one actuation element for carrying out several functions, wherein this handle should have a further improved operating ability compared to the known handle of this type.

This object is achieved by a handle for a medical instrument, having an actuation element arranged on the handle and being displaceable into at least first and second functional positions and being movable in a plane transverse to its displacement direction, in the first as well as the second functional position for carrying out a function, wherein a pivotable actuation lever is arranged on the handle, the actuation lever being coupled in movement to the actuation element for displacing the actuation element into the at least two functional positions. Advantageous further developments of this handle are to be deduced from the subsequent description as well as the drawings and claims. Herein, according to the invention, the features specified in the dependent claims and description, respectively, but also in a technically meaningful combination, further form the solution according to the invention.

The handle according to the invention for a medical instrument comprises an actuation element, which is arranged on the handle and which can be displaced at least into first and second functional positions and is movable in a plane transversely to its displacement direction in the first as well as the second functional position, for executing a function. Here, the functions which can be carried out by the actuation element in the first and second functional positions differ from one another. The type of these functions executable in the at least two functional positions by the actuation element is typically directed to the type of the medical instrument with which the handle according to the invention is applied and is basically infinite.

For example, with the functions executable with the actuation element in the instrument known from DE 10 2009 051 515 A1, it can be the case of the rotation of a shank arranged distally of the handle in a first functional position, and of the rotation of a tool arranged at the distal end of the shank in the second functional position. Moreover, the application of the handle according to the invention is also conceivable with such a medical instrument, with which a shank arranged distally of the handle is rotatable in a first functional position and a distal end section of this shank in a second functional position can be angled with respect to the remaining shank. Preferably, the actuation element, apart from the two functional positions, can also be displaced into such a position, in which no function can be carried out by it. Moreover, a design of the handle with which the actuation element is displaceable into more than two functional positions is conceivable.

The basic idea of the invention is to improve the operability of the handle by a pivotable actuation lever being arranged on the handle, the actuation lever being coupled in movement to the actuation element for displacing the actuation element into the at least two functional positions. The actuation lever is usefully designed as a two-sided lever, wherein a first lever arm of the actuation lever engages on the actuation element and a second lever arm, which is usefully longer than the first lever arm, serves for the manual force transmission onto the actuation lever. The movement coupling of the actuation lever to the actuation element is preferably such that the actuation element is displaced into a first functional position on pivoting the actuation lever in a first direction and is displaced into a second functional position on pivoting the actuation lever in a direction which is opposite to this. Compared to a direct, manual displacement of the actuation element into its two functional positions, the use of the actuation lever for this purpose has the advantage that the actuation element can be displaced with a significantly reduced force effort, so that the displacement of the actuation element into its functional positions is significantly easier.

Usefully, with the handle according to the invention, a displacement axis of the actuation element lies in a pivot plane of the actuation lever. That is, the pivot lever is arranged on the handle in a manner such that a pivot movement of the actuation lever and the displacement movement of the actuation element are effected in a common plane. This design has the advantage that a force component which acts directly in the displacement direction of the actuation element is exerted onto the actuation element, by the actuation lever when it is pivoted.

The coupling of movement of the actuation lever to the actuation element, with the handle according to the invention, is preferably effected by a positive fit between the actuation element and the actuation lever, the positive fit not being able to be released even with the common movement of the actuation lever and actuation element. In this context, according to an advantageous further development of the invention, one envisages the actuation element comprising a toothing, into which a corresponding toothing formed on the actuation lever engages. The toothed pairing of the actuation element and actuation lever is particularly advantageously designed similarly to a rack and pinion pairing, due to the linear movement guidance of the actuation element and the pivotally movable arrangement of the actuation lever about a pivot axis or rotation axis. Thus, a rack-shaped toothing can be formed on an outer side of the actuation element and a toothing which corresponds to a toothing of a section of a cog can be provided on an outer side of the actuation lever and preferably at the end of the second lever arm.

According to a further advantageous design, the actuation element of the handle according to the invention can comprise at least two recesses, into which a spring-biased locking element, fixedly arranged on the handle, engages in the at least two functional positions of the actuation element. This design serves for securing the actuation element with respect to an unintended linear movement, in its functional positions. Preferably, the actuation element comprises a further recess, which is arranged on the actuation element in a manner such that the locking element engages into it in a position, in which the actuation element executes no function. The locking element is preferably arranged on the handle in a manner such that a locking body of the locking element which rests on a spring element is pressed by the spring element in a direction normally to the displacement direction of the actuation element. The recesses formed on the actuation element hereby on the outer side of the actuation element usefully also extend normally to the displacement direction of the actuation element, wherein they are advantageously dimensioned such that the locking element engages into them with a positive fit. The recesses can simultaneously also be part of the previously described toothing for the engagement of the actuation lever.

Preferably, the actuation lever is arranged at a side of the handle, at which a fixedly arranged grip part of the handle extends essentially normally to a main axis of the handle. Here, a main axis of the handle is to be understood as an axis of the handle which extends in the direction of the longitudinal extension of a medical instrument, whose part forms the handle. That is, with respect to the medical instrument, in which the handle according to the invention is arranged, the fixedly arranged grip part is arranged in the manner of a pistol grip, wherein the actuation lever is preferably arranged in front of the grip part similarly to the trigger of a pistol. This design permits a simple accessibility of the actuation lever with a single-handed operation of the handle.

Advantageously, the actuation element of the handle is a rotation wheel which is axially displaceably arranged in the handle. That is, the rotation wheel is displaceable into its at least two functional positions in the direction of a central axis or rotation axis of the rotation wheel, wherein the function assigned to the respective functional position can be carried out by rotating the rotation wheel, in the two functional positions.

Further advantageously, the rotation wheel is preferably arranged on a sleeve. This sleeve is displaceable in the handle in the direction of its central axis and is rotatably mounted about its central axis. Several grooves, which are peripheral around the entire periphery of the sleeve, are formed on the outer periphery of the sleeve, preferably in a manner directly adjacent one another, and these grooves form a toothing. The corresponding toothing which is preferably formed on the actuation lever engages into this toothing. The number of grooves arranged on the outer side of the sleeve preferably corresponds to the number of functional positions of the actuation element formed by the sleeve and the rotation wheel which is arranged thereon. Thus, for example, three grooves can be formed on the sleeve, wherein in a first functional position of the actuation element, a first tooth of the toothing formed on the actuation lever engages into a first groove and after the pivoting of the actuation lever, which is entailed by displacement of the sleeve into a position in which the actuation cannot carry out a function, a second tooth of the toothing formed on the actuation lever engages into a second groove, and finally with a further pivoting of the actuation lever, by which the actuation element is displaced into a second functional position, a third tooth of the toothing formed on the actuation element engages into a third groove of the sleeve.

The grooves which are formed on the sleeve preferably have a rounded cross-sectional contour. Preferably, the profile of the grooves hereby corresponds to the profile of a flat segment of a circle. In particular, in combination with such grooves, the toothing on the actuation lever is advantageously formed by several rounded prominences which are directly adjacent one another in the pivot direction of the lever. Here, the cross-sectional profile of the prominences usefully essentially corresponds to the cross-sectional profile of the grooves formed on the sleeve. The rounded design of the grooves formed on the sleeve and the rounded design of the prominences formed on the actuation element, and which corresponds to this, permits an unproblematic rolling of the toothing arranged on the actuation lever on the toothing arranged on the sleeve during the simultaneous displacement of the sleeve or of the actuation element.

Usefully, the grooves formed on the sleeve also serve for fixing the actuation element in its functional positions. For this, the preferably provided, spring-biased locking element is advantageously arranged on the handle in a manner such that it engages in each case into one of the grooves formed on the sleeve, in the individual functional positions of the rotation wheel. In the handle, the locking element is preferably arranged on the side of the sleeve which is away from the actuation lever, wherein the spring element, on which the locking body of the locking element is supported, presses the looking body in the direction of the sleeve and thus in the direction of the groove arranged thereon.

With a design in which a rotation wheel forms the actuation element, the actuation lever can advantageously be articulated on the handle on a bow surrounding the rotation wheel at the outer side. The bow surrounds the rotation wheel at a certain distance usefully in the direction of the central axis of the rotation wheel and thus forms a mechanical protection for the rotation wheel. A longitudinal slot can be formed on the bow, in which slot the actuation lever at a distance to the rotation wheel and at a distance to the sleeve, on which the rotation wheel is arranged, is articulated in a manner such that the second lever arm of the actuation lever, which serves for the manual operation of the actuation lever, projects at the side of the bow which is away from the sleeve, out of this bow, and the toothing formed on the first lever arm of the actuation lever is engaged with the toothing formed on the sleeve.

In an alternative design for the movement coupling of the actuation lever and actuation element by toothings formed on the actuation lever and on the actuation element, the actuation lever can advantageously be designed in a fork-shaped manner and in one section branch into two limbs which are spaced from one another, which engage around or encompass a region of the actuation element and there are coupled in movement to the actuation element. The movement coupling of the actuation element to both limbs of the actuation lever can be effected by a groove extending over the entire periphery of the actuation element being formed on the outer side of the actuation element, into which groove a projection or pin arranged on the two limbs engages in each case.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
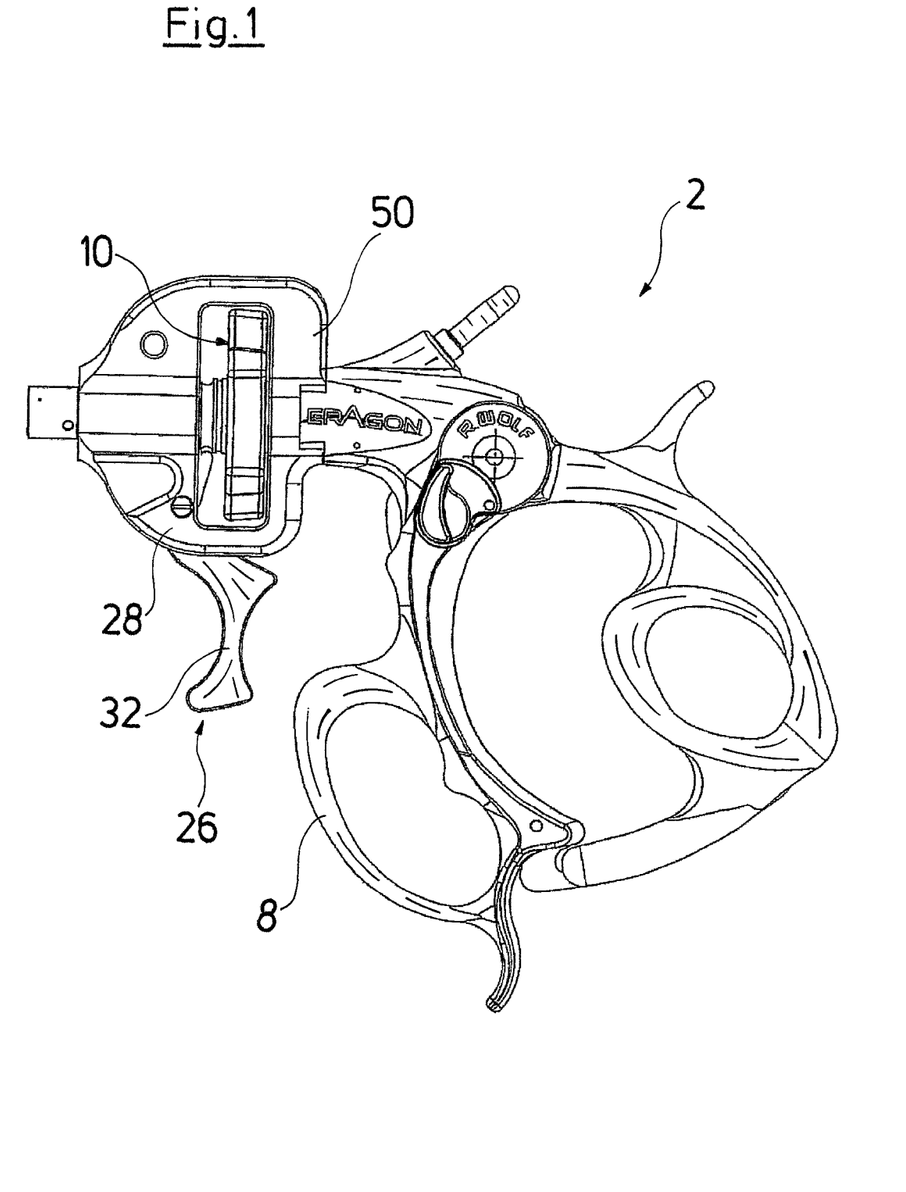
FIG. 1 is a lateral view of a handle for a medical instrument according to an embodiment of the invention.
Figure 2:
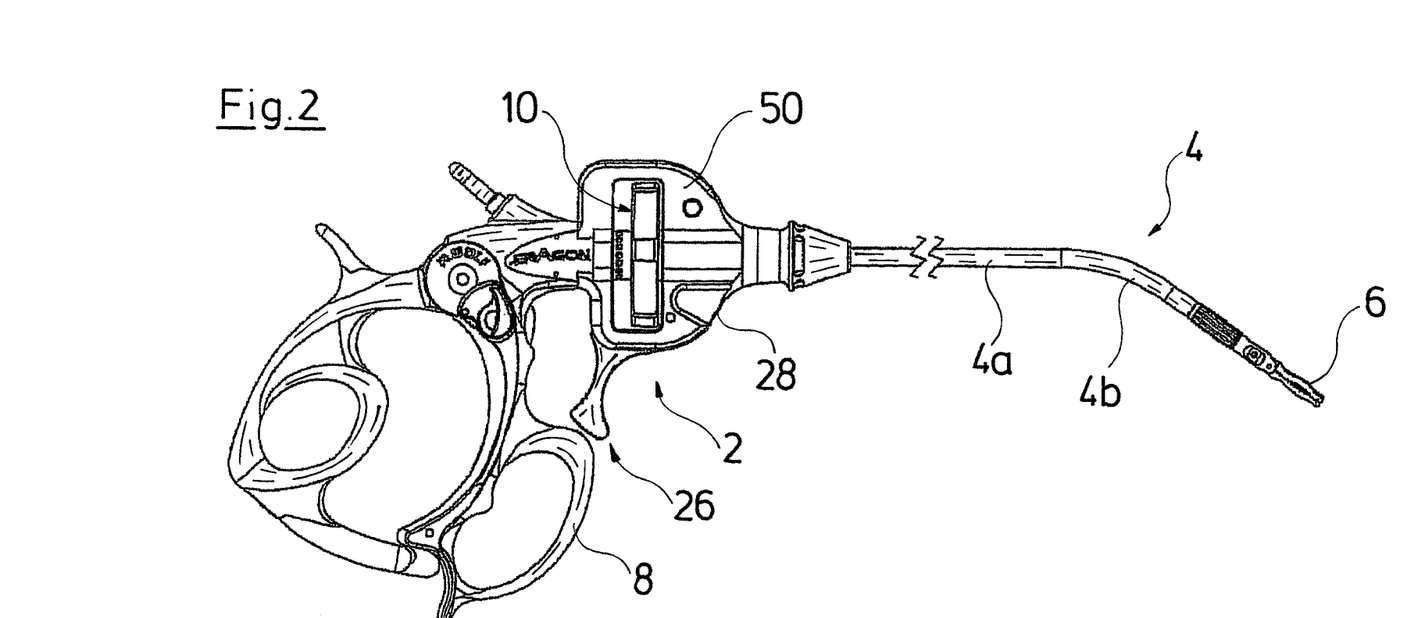
FIG. 2 is a lateral view of a medical instrument with the handle according to FIG. 1.
Figure 3:
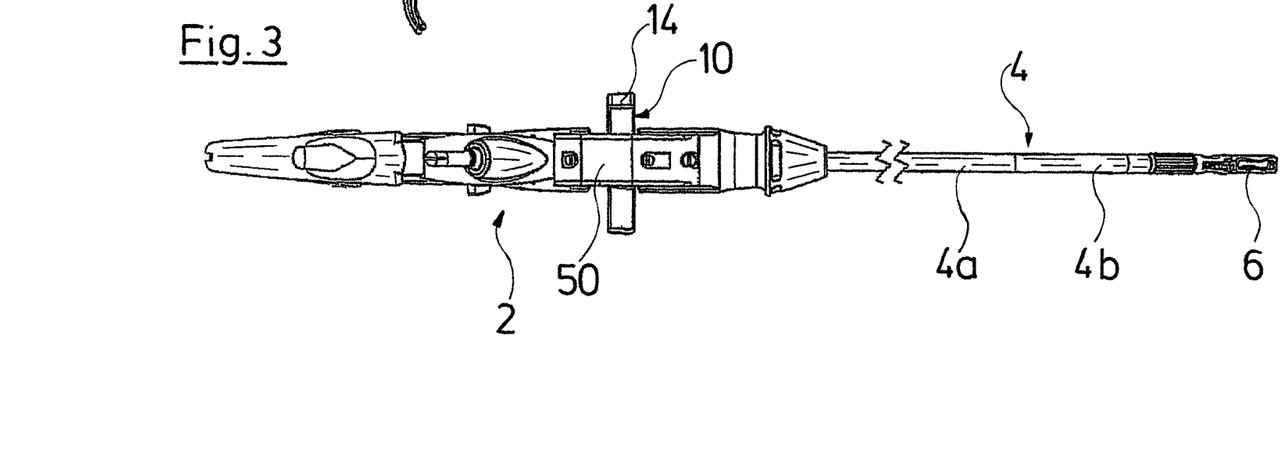
FIG. 3 is a plan view of the medical instrument according to FIG. 2.

The handle 2 represented in FIG. 1 is part of an endoscopic hollow shank instrument, as is represented in FIGS. 2 and 3. With this hollow shank instrument, a rigid hollow shank 4 is arranged distally of the handle 2 and comprises a straight, aligned hollow shank section 4a and a bent, distal shank section 4b which connects thereto obliquely to the shank section 4a. A tool 6 in the form of a gripping forceps is arranged at the distal end of the hollow shank 4. The hollow shank 4 is rotatably mounted on the handle 2 about the longitudinal axis of the proximal shank section 4a, and thus is rotatable relative to the handle 2. The tool 6 in turn is rotatable relative to the hollow shank 4.

The handle 2 comprises an actuation element 10 for the rotation of the hollow shank 4 and the tool 6, and this element extends between a grip part 8, which is fixedly arranged on the handle 2 and which extends essentially normally to a main axis A (FIG. 4) of the handle 2, and the distal end of the handle 2, on which the hollow shank 4 is led out of the handle 2. As can be particularly deduced from FIG. 5, the actuation element 10 is formed by a sleeve 12 and a rotation wheel 14 which is arranged thereon. Sections 12a and 12b of the sleeve 12 project beyond the face ends of the rotation wheel 14, in the direction of a central axis of the actuation element 10, whose position in the installed condition of the actuation element 10 in the handle 2 corresponds to the position of the main axis A of the handle. A toothing 16 is formed distally and a toothing 18 is formed proximally, on the face ends of the sleeve 12.

Figure 8:
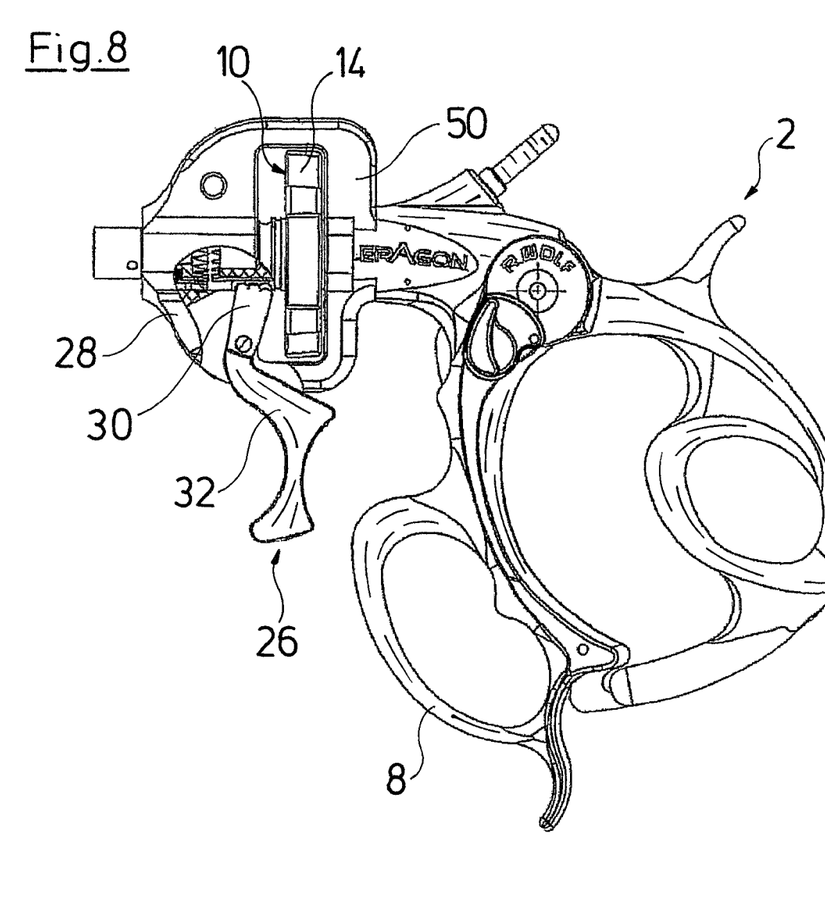
FIG. 8 is a partly sectioned representation of the handle according to FIG. 1 with the actuation element in a first functional position.
Figure 9:
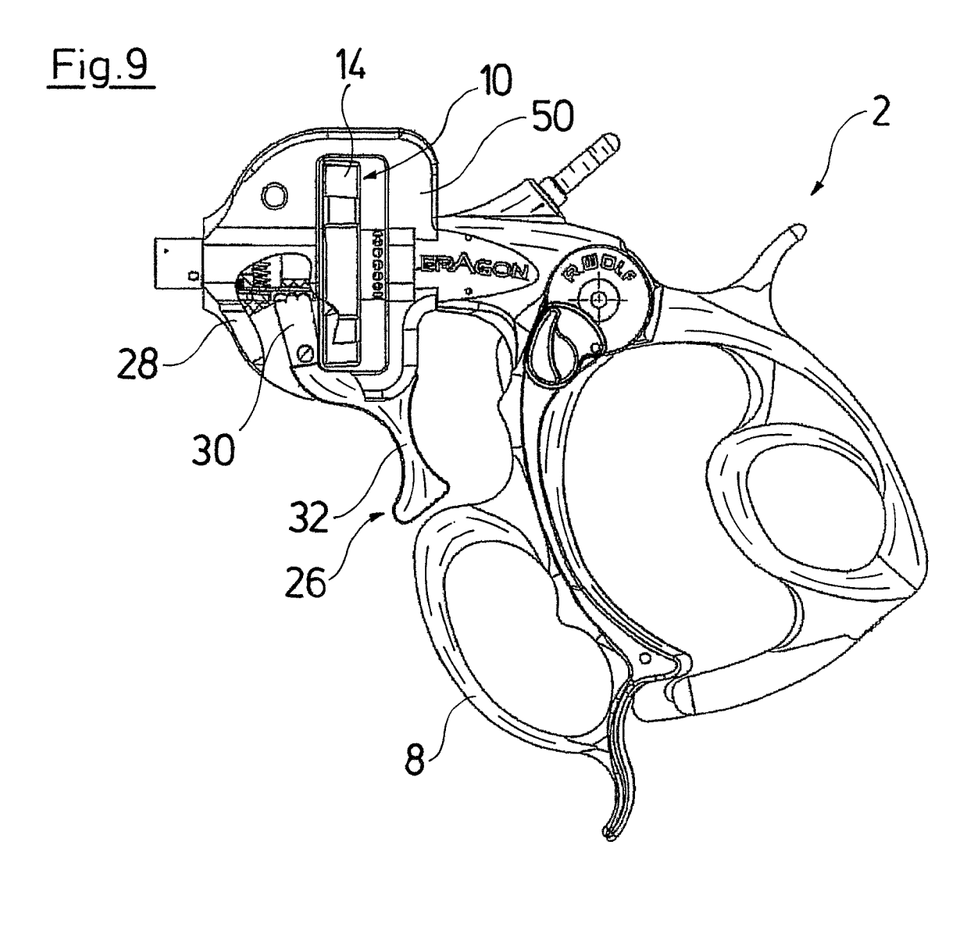
FIG. 9 is a partly sectioned representation of the handle according to FIG. 1 with the actuation element in a second functional position.

In the handle 2, the actuation element 10 is rotatably mounted about its central axis, i.e. about the main axis A of the handle, and in a limited region is displaceable in the direction of this central axis (see FIGS. 8 and 9). As can be deduced from FIG. 6, the axial displacement path of the actuation element 10 in the distal direction is limited by a hub 20, which is coupled in movement to the hollow shank 4. A hub 22 which is coupled in movement to an actuation rod of the tool 6, which rod is not shown in the drawings, limits the displacement path of the actuation element 10 in the proximal direction. The hub 20 and the hub 22 are each provided with a toothing. Thus, the hub 20 at its proximal end comprises a toothing 24, and the hub 22 at its distal end comprises a toothing which is not evident from the drawings.

Figure 6:
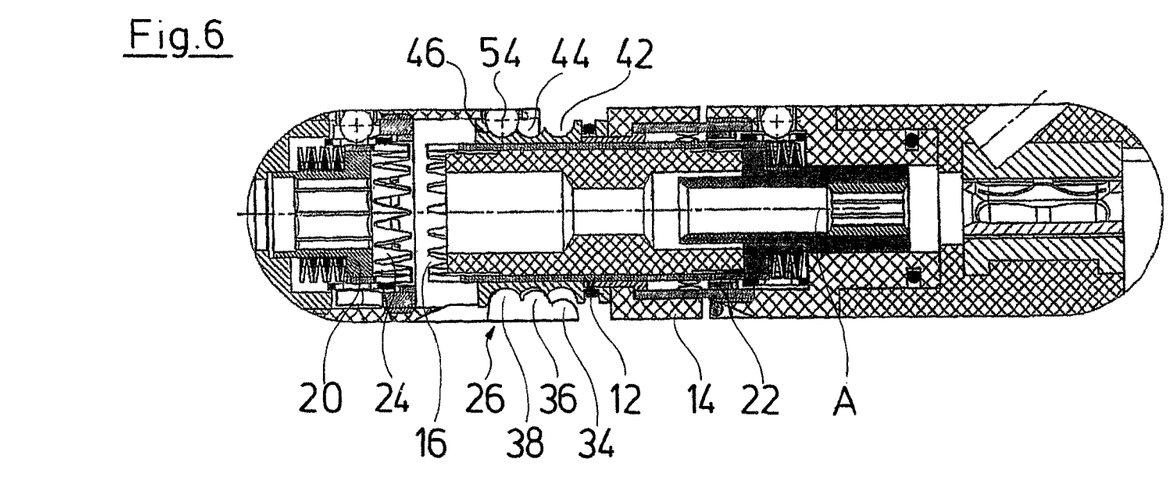
FIG. 6 is an enlarged detail Y of FIG. 4.

The actuation element 10 in FIGS. 6 and 8 is represented axially displaced into a proximal end position. Here, it is the case of a first functional position of the actuation element 10, in which the actuation element 10 is connected to the tool 6 in a rotationally fixed manner by engagement of the toothing 18 formed on the proximal side of the sleeve 12 into the toothing formed on the hub 22, so that the tool 6 can be rotated by rotating the rotation wheel 14 relative to the hollow shank 4. If the actuation element 10 is axially displaced in the distal direction, the toothing 16 formed distally on the sleeve 12, in a second functional position of the actuation element 10 engages into the toothing 24 of the hub 20. The actuation element 10 is connected to the hollow shank 4 in a rotationally fixed manner by this, so that the hollow shank 4 can be rotated by rotating the rotation wheel 14 relative to the handle 2.

The handle 10 comprises an actuation lever 26 for the axial displacement of the actuation element 10. This actuation lever 26 is pivotably mounted next to the hand grip 8, on a bow 28 encompassing the rotation wheel 14 of the actuation element 10. The actuation lever 26 is designed as a two-sided lever and comprises a first lever arm 30 and a second lever arm 32, wherein the first lever arm 30 serves for the subsequently explained movement coupling the actuation lever 26 to the actuation element 10, and the second lever arm 32 forms the operating part of the actuation lever 26.

Three projections, which are arranged in a row directly next to one another and which are formed by rounded prominences 34, 36 and 38 (see FIG. 6), are formed on the end of the first lever arm 30 of the actuation lever 26, the end being away from the second lever arm 32. Together, the prominences 34, 36 and 38 form a toothing. The sleeve 12 of the actuation element 10 in the section 12a distally of the rotation wheel 14 is surrounded by a ring 40, which is rigidly connected to the sleeve 12. Three grooves 42, 44 and 46, which are arranged in a row directly next to one another and which each extend over the entire outer periphery of the ring 40, are formed on the outer periphery of the ring 40. The grooves 42, 44 and 46 in each case have a rounded cross-sectional contour which corresponds to the cross-sectional contour of the prominences 34, 36 and 38, which are formed on the first lever arm 30 of the actuation lever 26. The grooves 42, 44 and 46 form a toothing, which is engaged by the toothing formed by the prominences 34, 36 and 38 on the part of the actuation lever 26. This is evident from FIGS. 4, 6, 8, and 9.

Figure 4:
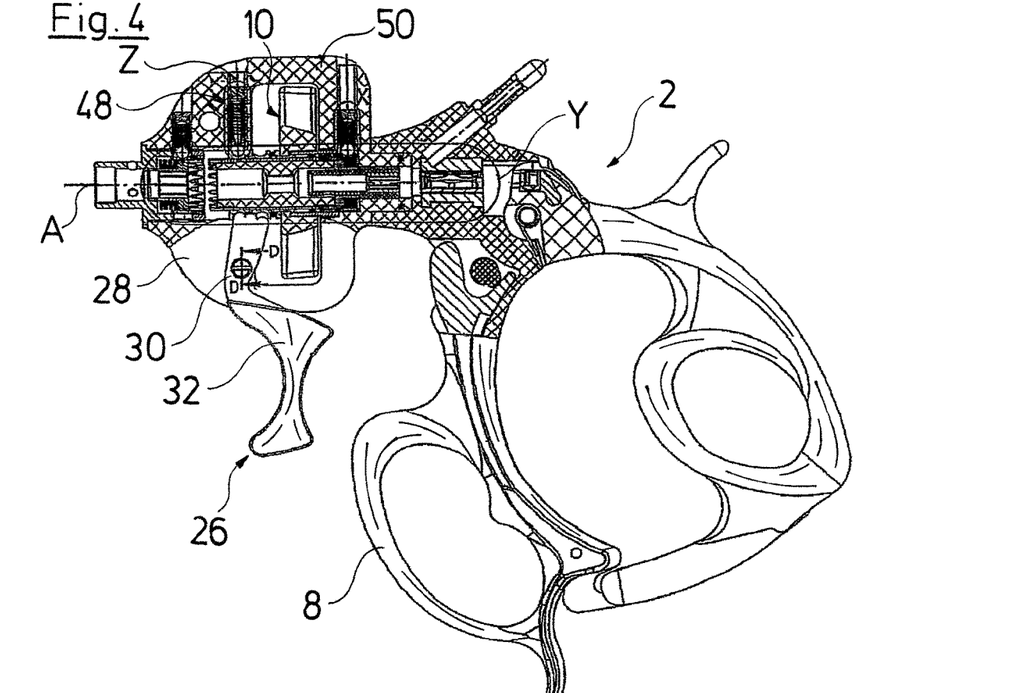
FIG. 4 is a partly sectioned representation of the handle according to FIG. 1.
Figure 5:
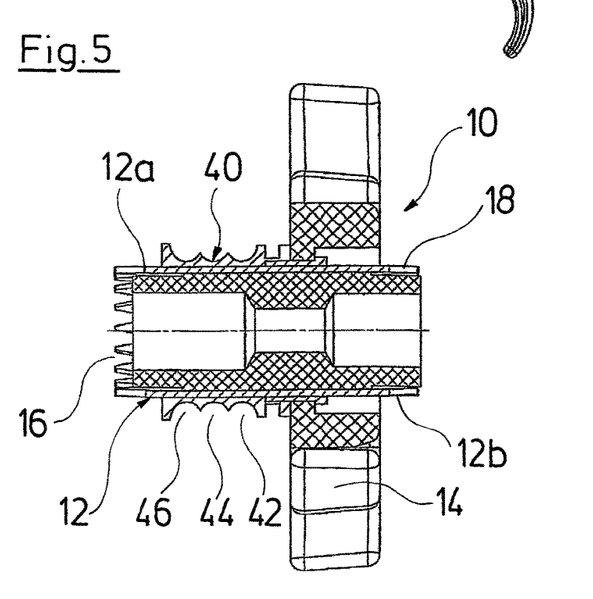
FIG. 5 is a sectioned lateral view of an actuation element of the handle according to FIG. 1.

In FIGS. 4, 6 and 8, the actuation lever 26 is pivoted in the distal direction into an end position, in which the prominence 38 distally arranged on the lever arm 30 engages into the groove 46 arranged distally on the ring 40. Here, the actuation element 10 is displaced as far as possible in the proximal direction, wherein the toothing 18 formed on the sleeve 12 engages into the toothing formed on the hub 22. The actuation element 10 is connected to the hub 22 in a rotationally fixed manner by this, and is entailed by this in a rotationally fixed manner to the tool 6.

If the actuation lever 26 is now pivoted in the proximal direction or in the direction of the grip part 8, the prominence 38 disengages and, in the course of the displacement of the actuation element 10 in the distal direction, the prominence 36 engages into the middle groove 44 formed on the ring 40. In this position, the actuation element 10 is neither coupled to the hub 22 nor to the hub 20.

If one pivots the actuation lever further in the direction of the grip part 8, the prominence 36 disengages and, in the course of the displacement of the actuation element 10 in the distal direction, the prominence 34 engages into the groove 42 formed proximally on the ring 40. The toothing 16, which is formed on the sleeve 12 of the actuation element 10, now engages into the toothing 24 formed on the hub 20, so that the actuation element 10 is connected to the hub 20 and thus to the hollow shank 4 of the medical instrument in a rotationally fixed manner (FIG. 9).

As described, the actuation element 10, due to the three prominences 34, 36 and 38 formed on the lever arm 30 of the actuation lever 26 and the three grooves 42, 44 and 46 which are formed on the ring 40 of the sleeve 12, can be displaced by the actuation lever 26 into three functional positions, specifically a first proximal functional position, in which the actuation element 10 is coupled to the tool 6 in a rotationally fixed manner, into a second functional position in which the actuation element is neither coupled to the tool nor to the hollow shank 4, and into a third distal functional position, in which the actuation element 10 is coupled to the hollow shank 4 in a rotationally fixed manner.

The handle 2 comprises a locking element 48 (FIG. 7), in order to be able to fix the actuation element 10 in each of the three functional positions. The locking element 48 is arranged on a bow 50, which surrounds the rotation wheel 14 of the actuation element 10 and which is arranged on the handle 2 lying directly opposite the bow 28. The locking element 48 consists essentially of a screw 52 with a hollow shank, in which a locking body 54 is supported on a helical spring 56 designed as a compression spring.

Figure 7:
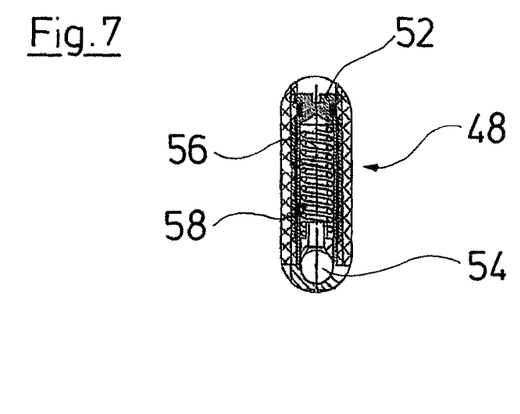
FIG. 7 is an enlarged detail Z of FIG. 4.

The locking element 48 is screwed in a threaded bore 58, which is formed on the bow 50, is open to the actuation element 10 and extends normally to the main axis A of the handle 2, radially in the direction of the section 12a of the sleeve 12. In each of the three functional positions of the actuation element 10, the locking body 54 of the locking element 48 diametrically opposite the actuation lever 26 engages into one of the grooves 42, 44 or 46 formed on the ring 40 of the sleeve 12.

It will be appreciated by those skilled in the art that changes could be made to the embodiments described above without departing from the broad inventive concept thereof.

It is understood, therefore, that this invention is not limited to the particular embodiments disclosed, but it is intended to cover modifications within the spirit and scope of the invention as defined by the appended claims.

The invention claimed is:

1. A handle for a medical instrument, the handle comprising:
    an actuation element arranged on the handle and displaceable along an axis between at least a first position and a second position, the actuation element being rotatable in a plane transverse to the axis in each of the at least first and second positions, wherein rotation of the actuation element in the first position effects a first operative function of the medical instrument and rotation of the actuation element in the second position effects a different, second operative function of the medical instrument;
    a pivotable actuation lever coupled in movement to the actuation element, the actuation element comprising grooves engaged by a toothing formed on the actuation lever, wherein pivoting of the actuation lever displaces the actuation element between the at least first and second positions; and
    a grip part fixedly arranged on the handle for holding the handle therefrom.

2. The handle according to claim 1, wherein the displacement axis of the actuation element extends along a pivot plane of the actuation lever.

3. The handle according to claim 1, further comprising a spring-biased locking element fixedly arranged on the handle, wherein the locking element engages into one of the grooves of the actuation element in the at least first and second positions of the actuation element.

4. The handle according to claim 1, wherein the grip part is fixedly arranged on one side of the handle and extends essentially normally to a main axis of the handle, and wherein the actuation lever is arranged at the one side of the handle with the grip part.

5. The handle according to claim 1, wherein the actuation element comprises a rotation wheel arranged in an axially displaceable manner in the handle.

6. The handle according to claim 5, wherein the rotation wheel is arranged on a sleeve.

7. The handle according to claim 6, wherein the sleeve comprises the grooves of the actuation element, the grooves extending around an entire periphery of the sleeve and being formed directly adjacent to one another, thereby forming a toothing.

8. The handle according to claim 7, wherein the grooves have a rounded cross-sectional contour.

9. The handle according to claim 1, wherein the toothing on the actuation lever is formed by a plurality of rounded prominences directly adjacent one another in a pivot direction of the actuation lever.

10. The handle according to claim 7, wherein a spring-biased locking element is arranged on the handle in a manner such that it engages a respective one of the grooves formed on the sleeve in the at least first and second positions of the rotation wheel.

11. The handle according to claim 5, wherein the actuation lever is articulated on a bow surrounding the rotation wheel on the outside.

* * * * *